(12) United States Patent
Diao et al.

(10) Patent No.: US 10,392,409 B2
(45) Date of Patent: Aug. 27, 2019

(54) FUNCTIONALIZED F-POSS MATERIALS AS ADDITIVES TO POLYMERS

(71) Applicant: NBD NANOTECHNOLOGIES, INC., Danvers, MA (US)

(72) Inventors: Cheng Diao, Auburndale, MA (US); Esra Altinok, Medford, MA (US); Bong June Zhang, Chestnut Hill, MA (US); Perry L. Catchings, Sr., Roxbury, MA (US)

(73) Assignee: NBD NANOTECHNOLOGIES, INC., Lexington, MA (US)

( * ) Notice: Subject to any disclaimer, the term of this patent is extended or adjusted under 35 U.S.C. 154(b) by 134 days.

(21) Appl. No.: 15/471,740

(22) Filed: Mar. 28, 2017

(65) Prior Publication Data

US 2017/0275437 A1    Sep. 28, 2017

Related U.S. Application Data

(60) Provisional application No. 62/313,948, filed on Mar. 28, 2016.

(51) Int. Cl.
*C07F 7/18* (2006.01)
*C08K 5/549* (2006.01)
*C07F 7/21* (2006.01)

(52) U.S. Cl.
CPC .............. *C07F 7/1804* (2013.01); *C07F 7/21* (2013.01); *C08K 5/549* (2013.01)

(58) Field of Classification Search
CPC ... C08K 9/04; C08K 5/549; C07F 7/21; C07F 7/1868
USPC ........................................................ 524/188
See application file for complete search history.

(56) References Cited

U.S. PATENT DOCUMENTS

| | | | | |
|---|---|---|---|---|
| 5,093,385 A | * | 3/1992 | Ali | C08F 293/00 522/27 |
| 6,367,167 B1 | * | 4/2002 | Krstic | A43B 5/02 36/25 R |
| 7,294,731 B1 | * | 11/2007 | Flynn | C07F 7/1804 556/427 |
| 9,193,829 B2 | * | 11/2015 | Ordonez | C08L 79/08 |
| 2006/0052623 A1 | | 3/2006 | Yoshida et al. | |
| 2016/0326191 A1 | * | 11/2016 | Warner | C07F 7/0876 |
| 2017/0204291 A1 | * | 7/2017 | Berry | C08G 77/045 |

FOREIGN PATENT DOCUMENTS

WO    2015179902 A1    12/2015

OTHER PUBLICATIONS

Mabry et al., Angew. Chem. Int. Ed., 47, 4137-4140, 2008. (Year: 2008).*

Search Report and Written Opinion for International Patent Application No. PCT/US2017/024528; dated Jun. 27, 2017.

Strachota et al., Formation of nanostructured epoxy networks containing polyhedral oligomeric silsesquioxane (POSS) blocks, Polymer, vol. 48, 2007, pp. 3041-3058.

* cited by examiner

*Primary Examiner* — Hui H Chin

(74) *Attorney, Agent, or Firm* — Barnes & Thornburg LLP; Jason Bernstein

(57) ABSTRACT

Functionalized fluoro polyhedral oligomeric silsesquioxane (F-POSS) materials as additives to improve liquid repellence of various polymers, the additive including at least one functionalized F-POSS material, wherein the functional group is at least one material selected from the group consisting of amines, isocyanates, epoxies, carboxylic acids, and esters.

18 Claims, 2 Drawing Sheets

FUNCTIONALIZED F-POSS MATERIALS AS ADDITIVES TO POLYMERS

CROSS-REFERENCE TO RELATED APPLICATION

This application claims benefit of U.S. provisional patent application 62/313,948, filed Mar. 28, 2016, entitled "FUNCTIONALIZED F-POSS MATERIALS AS ADDITIVES TO POLYMERS", and commonly assigned to the assignee of the present application, the disclosure of which is incorporated by reference in its entirety herein.

FIELD

The present disclosure relates, in exemplary embodiments, to functionalized fluoro polyhedral oligomeric silsesquioxane ("F-POSS") molecules as additives to polymers for providing superior hydrophobic and oleophobic properties.

SUMMARY

In exemplary embodiments, disclosed are functionalized F-POSS as additives to improve liquid repellence of various polymers. F-POSS itself has superior liquid repellence; however, due to its fully fluorinated structure, it has limited interaction with polymer matrix and tends to aggregate towards itself over time and elevated temperature, leading to decreased liquid repellence. Therefore, it would be desirable to introduce a degree of functionality into to F-POSS to mitigate these problems. The synthesized functionalized F-POSS as presently disclosed can significantly increase its miscibility with host polymers and stabilize itself within polymer matrix over time and elevated temperature due to the increased molecular interaction between introduced functionalities and the host polymers.

BRIEF DESCRIPTION OF THE DRAWINGS

The drawings disclose exemplary embodiments in which like reference characters designate the same or similar parts throughout the figures of which.

DETAILED DESCRIPTION

Figure 1:
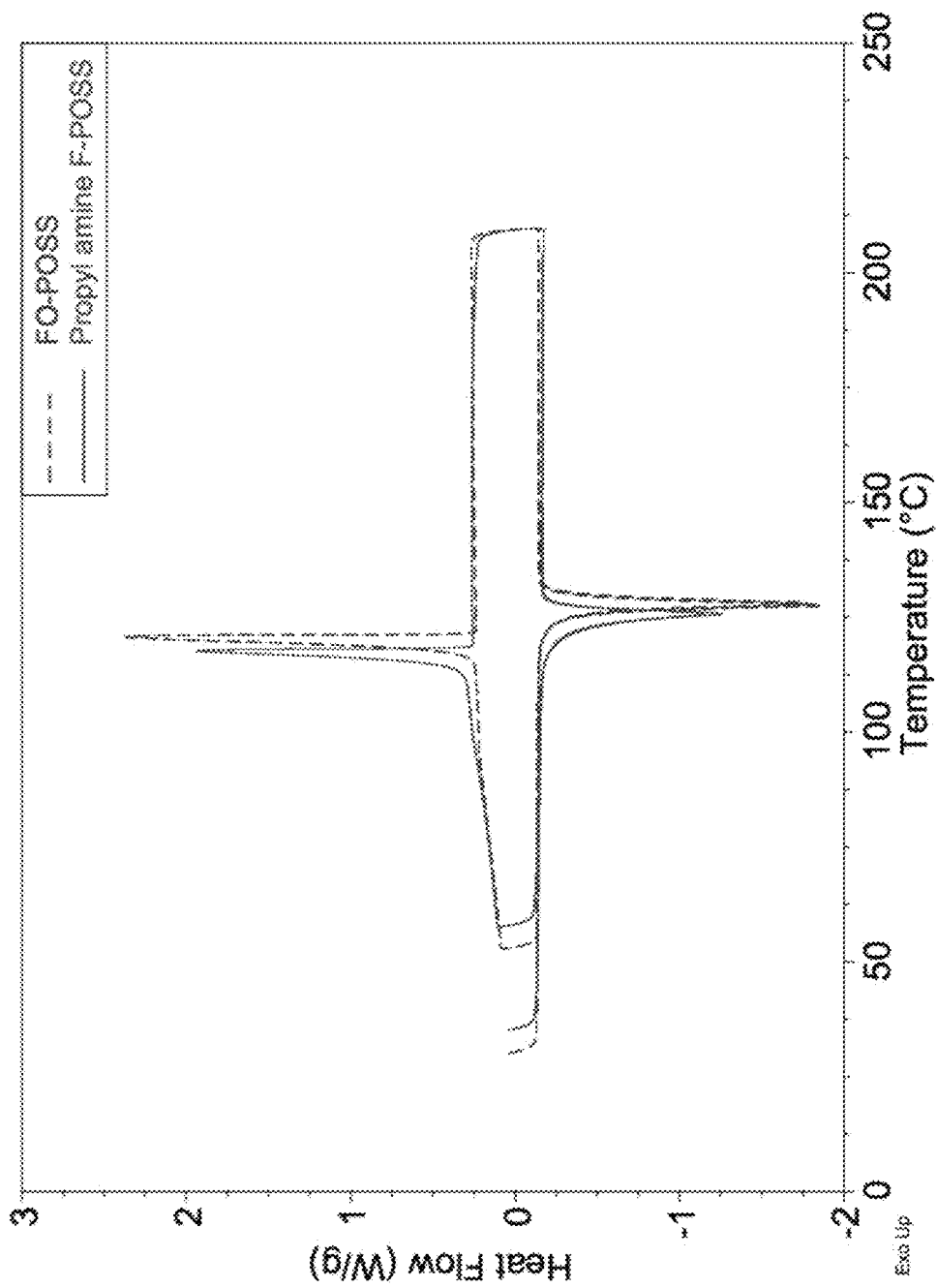
FIG. 1 is a graph of DSC characterization of FO-POSS and Propyl amine F-POSS according to Example 3.

Polymers are versatile materials and ubiquitously used due to their advantages over many other materials (metals, ceramics, etc.) properties, such as, light weight, easy processing, cost, and so on. As the applications for polymers expand at an increasingly faster rate, various new applications require superior properties, such as outstanding durability, high mechanical properties, high liquid repellence, etc. Among all these properties, high liquid repellence is one of the most important properties and recently has been attracting substantial attention.

Generally, in comparison to metals and ceramics, polymers have much lower surface tension due to less polar atoms and bonds in its polymer structures. Their surface tension is much lower than surface tension of water that is 72 N/m, therefore, making most polymers inherently hydrophobic. Nevertheless, their surface tension is higher than most of the oil based liquids (~25 N/m), making it oleophilic. Many novel applications require polymers to be both more hydrophobic and oleophobic, therefore, modifications are required to decrease surface tension of polymers.

There are two main approaches to decrease surface tension of polymers: surface modification and additives. Many studies have shown that surface modification can dramatically decrease polymers' surface tension, however, the manufacturing process is costly and the surface's durability is low, especially under friction. Traditional low surface tension additives, such as PTFE, PFA, PVDF, cannot effectively decrease surface tension due to their low miscibility with the host materials. Usually, large phase separation is observed, which can barely decrease the surface tension. Meanwhile, their high molecular weight or large particle size prevents them from blooming to the surface. Therefore, a novel approach is expected to address the above problems. F-POSS can improve polymer's liquid repellence for several reasons. First, F-POSS (molar mass=3993.54 g/mol, ρ=2.067 g/cm3) is one of the most hydrophobic/omniphobic solid material currently known. On smooth surfaces, it exhibits hexadecane contact angles above 80°, among the most oleophobic materials in its class. Second, F-POSS exhibits excellent thermal stability up to about 309° C. and only evaporates above about 309° C. Third, F-POSS has melting temperature of 126° C.; therefore, F-POSS is much easier to be integrated into host polymers at their extrusion temperatures. Moreover, after compounded with polymers, some F-POSS material can then migrate to the polymer-air interface to form a low surface tension layer due to its limited miscibility with the host materials. The F-POSS beneath the surface can also replenish the surface layer in a self-healing manner.

Limited miscibility of F-POSS, nevertheless, drives itself to aggregate over time and at elevated temperature, leading to decreased liquid repellence. Therefore, functionalized F-POSS is proposed to increase its molecular interaction with the matrix polymers and to stabilize its distribution over time and at elevated temperature. In exemplary embodiments, various functionalized F-POSS, such as, amine functionalized F-POSS, isocyanate functionalized F-POSS, epoxy functionalized F-POSS, carboxylic acid functionalized F-POSS, ester functionalized F-POSS, are proposed to be synthesized and used as effective additives to increase its miscibility and improve liquid repellence of polymers, including, polyurethanes, polyamides, polyacrylates, polyolefins, polyesters, polyethers, fluorinated polymers (PTFE, PFA, PVDF, FEP, ETFE, etc.), polystyrene, etc.

In exemplary embodiments, the functionalized F-POSS has the formula shown in Formula [1]:

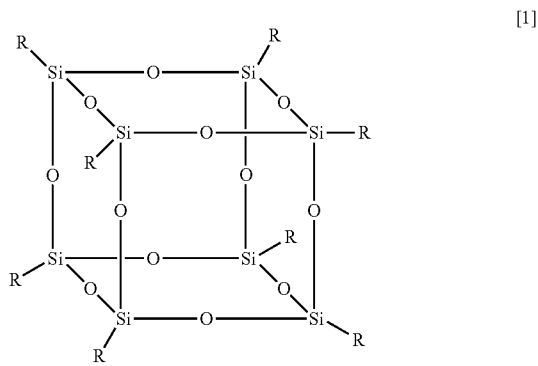

[1]

in which:

R=$R_f$ or $R_f'$ $R_f$=—(CH$_2$)$_n$—(CF$_2$)$_q$—CF$_3$ (where, in exemplary embodiments, n is between 0 and 5, and in other exemplary embodiments, n=2; and where, in exemplary embodiments, q is between 0 and 15, and in other exemplary embodiments, q is either 6 or 8);

$R_f'$=—(CH$_2$)$_m$—X (where m is between 0 and 15); and

X is a group selected from the group consisting of —NH$_2$ (either primary, secondary or tertiary amines), —NCO, —COOH, —CO—O—, epoxy, —OH, —S—CN, —(C$_6$H$_6$), —N(CH$_3$)$_3$$^+$Cl$^-$, halogen (e.g., —Cl, Br, F, or I), —SH, cyano, alkoxy, aryloxy, N-carbamyl, thiocarbamyl, amido, sulfinyl, sulfonyl, sulfonamido, alkylthio, arylthio, heterocyclic, heteroaryl, heterocycloalky, quaternary ammonium, cycloalkyl, carbonyl, oxo, nitro, alkenyl, and alkynyl groups, and the ratio of $R_f$:$R_f'$=7:1, 6:2, 5:3, 4:4, 3:5, 2:6, or 1:7.

Functionalized F-POSS is synthesized from functionalized silane and fluorinated alkylsilane (FAS).

Fluorinated alkylsilane (FAS) molecular structure is shown in Formula [2]:

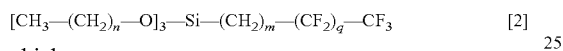

[2]

in which:

in exemplary embodiments, n is between 0 and 15, in other exemplary embodiments, n can be a different number.

in exemplary embodiments, m is from 0 to 5, in other exemplary embodiments, m is 2, and in exemplary embodiments, q is from 0 to 15, in other exemplary embodiments, m is 6 or 8.

Functionalized silane molecular structure is shown in Formula [3]:

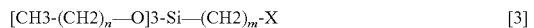

[3]

in which:

in exemplary embodiments, n is between 0 and 15, in other exemplary embodiments, n can be a different number;

m is between 0 and 18; and

X is —NH$_2$ (primary, secondary or tertiary amines), —NCO, —COOH, —CO—O—, epoxy, —OH, —S—CN, —(C$_6$H$_6$), —N(CH$_3$)$_3$$^+$Cl$^-$, halogen (e.g., —Cl, Br, F, or I), —SH, cyano, Alkoxy, aryloxy, N-carbamyl, thiocarbamyl, amido, sulfinyl, sulfonyl, sulfonamido, alkylthio, arylthio, heterocyclic, heteroaryl, heterocycloalky, quaternary ammonium, cycloalkyl, carbonyl, oxo, nitro, alkenyl, or alkynyl.

In one exemplary embodiment, a functionalized F-POSS is synthesized as follows:

a) Fluorinated alkylsilane (FAS) and functionalized silane precursors are mixed at the mole ratio of: 7:1, 6:2, 5:3, 4:4, 3:5, 2:6, or 1:7;

b) Precursors with one of the above ratios are added into reaction solvents;

c) Aqueous KOH solution is used as catalyst;

d) Reaction is conducted under stirring at room temperature overnight;

e) Final product is collected and washed with hot ethanol and then dried overnight.

In exemplary embodiments, the additive functionalized F-POSS and polymer are compounded according to the following recipes:

a) Functionalized F-POSS: 0.05 wt %-50 wt % b) Polymers: 99.5% wt-50 wt %

In one exemplary embodiment, with the above ratios, functionalized F-POSS and polyurethanes are compounded in a twin-screw extruder at the host polymer's processing temperature.

In one exemplary embodiment, a polymer formulation is provided comprising a polymer as described herein and a functionalized F-POSS material as described herein.

In one exemplary embodiment, the functionalized F-POSS material can be used as an additive in a polymer formulation in the manufacture of cleated shoes, such as, but not limited to, soccer (a/k/a football) shoes, to prevent or reduce mud buildup on the shoe.

In exemplary embodiments of a method of forming functionalized F-POSS materials, in order for the formed F-POSS amine material to become a solid powder, the reaction is performed with an alkane, such as, but not limited to, heptane, octane, pentane, combinations of at least two of the foregoing, or the like, in combination with an ethanol/isopropyl alcohol mixture.

The following examples are set forth for purposes of illustration only. Parts and percentages appearing in such examples are by weight unless otherwise stipulated.

EXAMPLES

Example 1

Synthesis of Propyl Amine F-POSS 1) 4 ml of 1H,1H,2H,2H-Perfluorooctyltriethoxysilane and (3-Aminopropyl)triethoxysilane was mixed in a flask at the mole ratio of 7:1.

2) Precursor mixture was added into 11 ml an ethanol/heptane mixture at the ratio of 10:1.

3) 400 ul of 0.01 g/ml KOH solution was added as catalyst.

4) The reaction was stirred for 16 hours at room temperature.

5) Precipitated white power was collected and then purified by washing with ethanol. Pure white solid was obtained after drying under vacuum for 16 hours.

Example 2

Thermoplastic Polyurethane/Propyl Amine F-POSS Nano-Composite Preparation 1) 4 g of thermoplastic polyurethane (TPU) (95 wt %) and propyl amine F-POSS (5 wt %) were compounded in a bench top twin screw mini-compounder at speed of 100 rpm for 5 min at 210° C.

2) The compounded pellets were then injection molded into small bars for contact angle measurement.

Example 3

Differential Scanning Calorimetry (DSC) Characterization of Propyl amine F-POSS 5 mg of fluoro octyl polyhedral oligomeric silsesquioxane (FO-POSS) and Propyl amine F-POSS were performed for DSC characterization with results shown in FIG. 1. FO-POSS had a melting temperature of 127° C. and propyl amine POSS had a melting temperature of 124° C. The relatively lower melting temperature of propyl amine POSS was considered originating from the slightly irregular structure caused by the shorter chain of propyl amine silane. Moreover, both FO-POSS and propyl amine POSS showed excellent thermal stability up to the compounding temperature, which was demonstrated by the crystallization peak and perfect overlay of first and second heating cycle.

Figure 2:
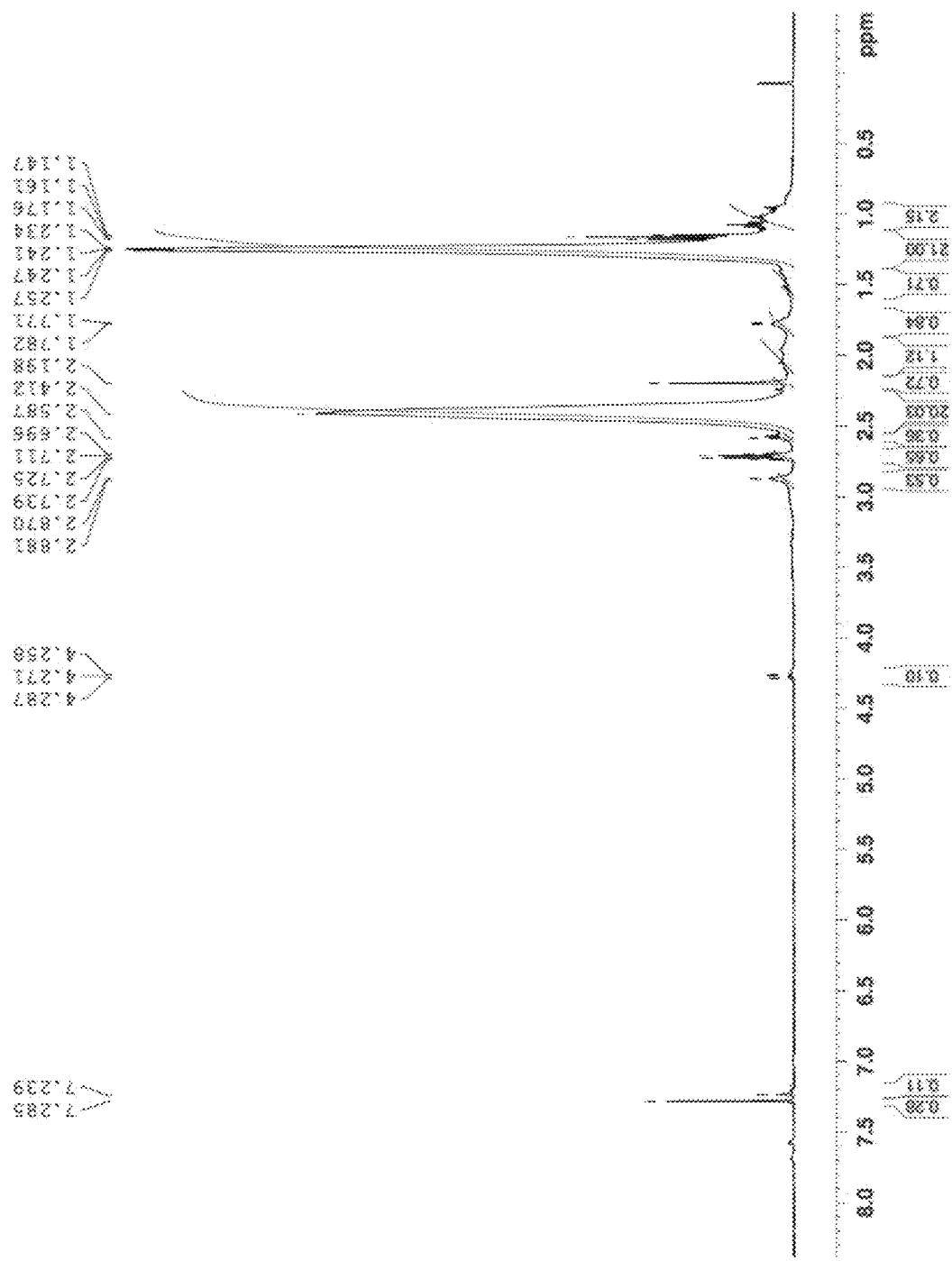
FIG. 2 is a graph of NMR characterization of Propyl amine F-POSS according to Example 3.

The nuclear magnetic resonance spectroscopy (NMR) characterization of Propyl amine F-POSS is shown in FIG. 2.

Example 4

Contact Angle Measurement

Both TPU/5% FO-POSS and TPU/5% Propyl amine F-POSS samples were conducted for contact angle measurements with data summarized in Table 1 and Table 2.

TABLE 1

Contact angle measurements of TPU/5% FO-POSS

| TPU/5% FO-POSS | Static Contact Angle (degrees) | |
|---|---|---|
| | H$_2$O | Hexadecane |
| Before annealing | 114 ± 0.5 | 69 ± 1.5 |
| Anneal @ 140° C. 1 h | 110 ± 1.7 | 52 ± 1 |
| Anneal @ 200° C. 10 min | 94 ± 1.7 | 47 ± 0.5 |

TABLE 2

Contact angle measurements of TPU/5% Propyl amine-POSS

| TPU/5% Propyl amine F-POSS | Static Contact Angle (degrees) | |
|---|---|---|
| | H$_2$O | Hexadecane |
| Before annealing | 114 ± 1 | 72 ± 3 |
| Anneal @ 140° C. 1 h | 116 ± 1 | 72 ± 1 |
| Anneal @ 200° C. 10 min | 111 ± 0.8 | 68 ± 1 |

Before annealing, both TPU/5% FO-POSS and TPU/5% Propyl amine F-POSS illustrate similar water and hexadecane contact angle. Nevertheless, upon thermal annealing, both water and hexadecane contact angle of TPU/5% FO-POSS decreased by 20°, which is believed to be due to FO-POSS aggregation on the surface. In comparison, the water and hexadecane contact angle of TPU/5% Propyl amine F-POSS was well preserved during annealing at high temperature, demonstrating the increased molecular interaction between TPU and amine functionalized POSS that effectively prevents the phase aggregation.

The following numbered clauses include embodiments that are contemplated and non-limiting.

Clause 1: An additive to a polymer, comprising: at least one functionalized F-POSS material, wherein the functional group is at least one material selected from the group consisting of amines, isocyanates, epoxies, carboxylic acids, and esters.

Clause 2: The additive of Clause 1, wherein the polymer is at least one polymer selected from the group consisting of polyurethanes, polyamides, polyacrylates, polyolefins, polyesters, polyethers, fluorinated polymers, and polystyrenes.

Clause 3: The additive of Clause 1, wherein the mole ratio of fully fluorinated chain to the polar functionalities is either 7:1, 6:2, 5:3, 4:4, 3:5, 2:6, or 1:7.

Clause 4: A polymer formulation, comprising:
a. at least one polymer material selected from the group consisting of polyurethanes, polyamides, polyacrylates, polyolefins, polyesters, polyethers, fluorinated polymers, and polystyrenes; and b. an additive comprising at least one functionalized F-POSS material, wherein the functional group is at least one material selected from the group consisting of amines, isocyanates, epoxies, carboxylic acids, and esters.

Clause 5: A functionalized F-POSS material, comprising the structure shown in Formula 1:

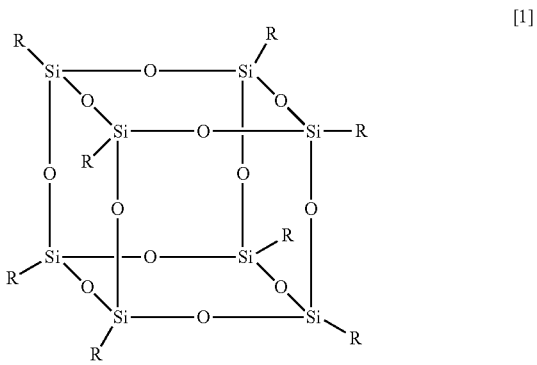

[1]

Clause 6: The functionalized F-POSS material of Clause 5,
a. wherein R is either $R_f$ or $R_f'$,
b. wherein $R_f$ is —(CH$_2$)$_n$—(CF$_2$)$_q$—CF$_3$ where n is between 0 and 5, and where q is between 0 and 15,
c. wherein $R_f'$ is —(CH$_2$)$_m$—X, where m is between 0 and 15, and
d. wherein X is a group selected from the group consisting of —NH$_2$ (either primary, secondary or tertiary amines), —NCO, —COOH, —CO—O—, epoxy, —OH, —S—CN, —(C$_6$H$_6$), —N(CH$_3$)$_3$$^+$Cl$^-$, halogen, —SH, cyano, alkoxy, aryloxy, N-carbamyl, thiocarbamyl, amido, sulfinyl, sulfonyl, sulfonamido, alkylthio, arylthio, heterocyclic, heteroaryl, heterocycloalky, quaternary ammonium, cycloalkyl, carbonyl, oxo, nitro, alkenyl, and alkynyl groups.

Clause 7: The functionalized F-POSS material of Clause 6, wherein the ratio of $R_f$:$R_f'$ is either 7:1, 6:2, 5:3, 4:4, 3:5, 2:6, or 1:7.

Clause 8: The functionalized F-POSS material of Clause 6, wherein $R_f$ is —(CH$_2$)$_n$—(CF$_2$)$_q$—CF$_3$ and where n is 2.

Clause 9: The functionalized F-POSS material of Clause 6, wherein $R_f$ is —(CH$_2$)$_n$—(CF$_2$)$_q$—CF$_3$ and where q is either 6 or 8.

Clause 10: A functionalized F-POSS material synthesized from functionalized silane and fluorinated alkylsilane (FAS).

Clause 11: The functionalized F-POSS material of Clause 5, wherein the material after annealing has a water contact angle and a hexadecane contact angle of about 20% less than that of the material prior to annealing.

Clause 12: A fluorinated alkylsilane (FAS) molecule comprising the structure shown in Formula [2]:

$$[CH_3—(CH_2)_n—O]_3—Si—(CH_2)_m—(CF_2)_q—CF_3 \quad [2]$$

wherein
n is between 0 and 15,
m is from 0 to 5, and,
q is from 0 to 15.

Clause 13: A functionalized silane molecule, comprising the structure shown in Formula [3]:

$$[CH3-(CH2)_n—O]3-Si—(CH2)_m-X \quad [3]$$

wherein
n is between 0 and 15,
m is between 0 and 18; and
X is a group selected from the group consisting of —NH$_2$ (primary, secondary or tertiary amines), —NCO, —COOH, —CO—O—, epoxy, —OH, —S—CN, —(C$_6$H$_6$), —N(CH$_3$)$_3$$^+$Cl$^-$, halogen (e.g., —Cl, Br, F, or I), —SH, cyano, alkoxy, aryloxy, N-carbamyl, thiocarbamyl, amido, sulfinyl, sulfonyl, sulfonamido, alkylthio, arylthio, heterocyclic, heteroaryl, heterocycloalky, quaternary ammonium, cycloalkyl, carbonyl, oxo, nitro, alkenyl, and alkynyl.

Clause 14: A method for synthesizing a functionalized F-POSS comprising:
mixing fluorinated alkylsilane (FAS) and at least one functionalized silane precursor at a mole ratio of either 7:1, 6:2, 5:3, 4:4, 3:5, 2:6, or 1:7;
adding the mixture of step a) into a solvent at a mole ratio of either 7:1, 6:2, 5:3, 4:4, 3:5, 2:6, or 1:7;
adding aqueous KOH solution as a catalyst;
stirring the above at room temperature; and,
collecting precipitated final product.

Clause 15: The method of Clause 14, further comprising step f) washing the precipitated final product with ethanol and then drying.

Clause 16: The method of Clause 14, wherein the additive functionalized F-POSS and polymer are present in the following amounts:
functionalized F-POSS: 0.05 wt %-50 wt % and,
polymers: 99.5% wt-50 wt %.

Clause 17: The method of Clause 14, wherein the solvent precursor is a combination of an alkane and a mixture of ethanol and isopropyl alcohol.

Clause 18: The method of Clause 17, wherein the alkane is selected from the group consisting of heptane, octane, pentane and combinations of at least two of the foregoing.

Clause 19: A method of forming a composite, comprising:
a. providing a material formed according to the method of Clause 14 and a thermoplastic polyurethane; and,
b. compounding the foregoing in a compounder to form pellets.

Clause 20: An additive in a polymer formulation used in the manufacture of shoes, the additive being made according to the method of Clause 14.

Although only a number of exemplary embodiments have been described in detail above, those skilled in the art will readily appreciate that many modifications are possible in the exemplary embodiments without materially departing from the novel teachings and advantages. Accordingly, all such modifications are intended to be included within the scope of this disclosure as defined in the following claims.

While the methods, equipment and systems have been described in connection with specific embodiments, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect.

As used in the specification and the appended claims, the singular forms "a," "an" and "the" include plural referents unless the context clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods, equipment and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods, equipment and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

What is claimed is:
1. A method for synthesizing a functionalized F-POSS comprising:
   a) mixing a fluorinated alkylsilane (FAS) and at least one functionalized silane at a mole ratio of either 7:1, 6:2, 5:3, 4:4, 3:5, 2:6, or 1:7;
   b) adding the mixture of step a) into a solvent;
   c) adding an aqueous KOH solution as a catalyst to the solvent;
   d) stirring the above at room temperature; and,
   e) collecting precipitated final product.

2. The method of claim 1, further comprising step f) washing the precipitated final product with ethanol and then drying.

3. The method of claim 1, comprising combining the functionalized F-POSS and a polymer in the following amounts:
   f) functionalized F-POSS: 0.05 wt %-50 wt % and,
   g) polymers: 99.5% wt-50 wt %.

4. The method of claim 1, wherein the solvent is a combination of an alkane and a mixture of ethanol and isopropyl alcohol.

5. The method of claim 4, wherein the alkane is selected from the group consisting of heptane, octane, pentane and combinations of at least two of the foregoing.

6. A method of forming a composite, comprising:
   h) providing the functionalized F-POSS formed according to the method of claim 1 and a thermoplastic polyurethane; and, i) compounding the foregoing in a compounder to form pellets.

7. An additive in a polymer formulation used in the manufacture of shoes, the additive being made according to the method of claim 1.

8. The method of claim 3, wherein the polymer is at least one polymer selected from the group consisting of polyurethanes, polyamides, polyacrylates, polyolefins, polyesters, polyethers, fluorinated polymers, and polystyrenes.

9. The method of claim 8, wherein the polymer is a polyurethane.

10. The method of claim 1, wherein the functionalized silane comprises an amine, an isocyanate, an epoxy, a carboxylic acids, or an ester.

11. The method of claim 10, comprising combining the functionalized F-POSS and a polymer wherein the polymer is at least one polymer selected from the group consisting of polyurethanes, polyamides, polyacrylates, polyolefins, polyesters, polyethers, fluorinated polymers, and polystyrenes.

12. The method of claim 11, wherein the polymer is a polyurethane.

13. The method of claim 12, wherein the functionalized silane comprises an amine.

14. The method of claim 1, wherein the functionalized silane is of the formula

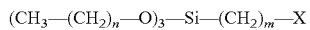

$(CH_3-(CH_2)_n-O)_3-Si-(CH_2)_m-X$ wherein:

n is 0 to 15, m is 1 to 18; and

X is selected from the group consisting of $-NH_2$, $-NCO$, $-COOH$, $-COO^-$, epoxy, $-OH$, $-SCN$, $-(C_6H_6)$, $-N(CH_3)_3{}^+Cl^-$, halogen, $-SH$, cyano, alkoxy, aryloxy, N-carbamyl, thiocarbamyl, amido, sulfinyl, sulfonyl, sulfonamido, alkylthio, arylthio, heterocyclic, heteroaryl, heterocycloalkyl, quaternary ammonium, cycloalkyl, carbonyl, oxo, nitro, alkenyl, and alkynyl.

15. The method of claim 14, wherein X is $-NH_2$.

16. The method of claim 1, wherein the functionalized silane is (3-aminopropyl)triethoxysilane.

17. The method of claim 16, wherein the FAS is 1H,1H,2H,2H-perfluorooctyltriethoxysilane.

18. The method of claim 17, wherein the method further comprises compounding the functionalized F-POSS with a thermoplastic polyurethane.

* * * * *